United States Patent [19]

Lodde et al.

[11] Patent Number: 5,052,930
[45] Date of Patent: Oct. 1, 1991

[54] DENTAL IMPLANT AND METHOD OF IMPLANTATION

[76] Inventors: Jean-Pierre Lodde, 47 Chemin De Rozarglin; Philippe Guennal, 1 rue Saint Marc, both of 29000 Quimper, France

[21] Appl. No.: 489,691

[22] Filed: Mar. 7, 1990

Related U.S. Application Data

[63] Continuation-in-part of Ser. No. 442,471, Nov. 22, 1989, abandoned, which is a continuation of Ser. No. 356,271, May 24, 1989, abandoned.

[51] Int. Cl.$^5$ .................................................. A61C 8/00
[52] U.S. Cl. ...................................... 433/173; 433/176
[58] Field of Search ............... 433/169, 173, 174, 175, 433/176, 201.1

[56] References Cited

U.S. PATENT DOCUMENTS

| | | | |
|---|---|---|---|
| 3,082,525 | 3/1963 | Christensen | 433/174 |
| 3,579,829 | 5/1971 | Sampson | 433/173 |
| 4,702,697 | 10/1987 | Linkow | 433/173 |

FOREIGN PATENT DOCUMENTS

| | | | |
|---|---|---|---|
| 2237598 | 2/1974 | Fed. Rep. of Germany | 433/176 |
| 3732128 | 4/1989 | Fed. Rep. of Germany | 433/173 |
| 2138224 | 5/1973 | France | 433/176 |
| 560230 | 4/1957 | Italy | 433/173 |

OTHER PUBLICATIONS

Integral Biointegrated Dental Implant System: Instructions for Use.
Techmedica, TiMesh, Inc., Vitek Inc. advertisements.

*Primary Examiner*—John J. Wilson
*Attorney, Agent, or Firm*—Warren L. Franz

[57] ABSTRACT

A juxtaosseous dental implant for application to the mandible or maxilla has a trucated conical post projecting upward from a spider-like base having a central hub portion placed in shielding position over the center of the implantation site and at least three spoke-like branches screwed into the bone at points removed from the site center, thereby providing energy dissipating, multi-directional, three point attachment.

16 Claims, 3 Drawing Sheets

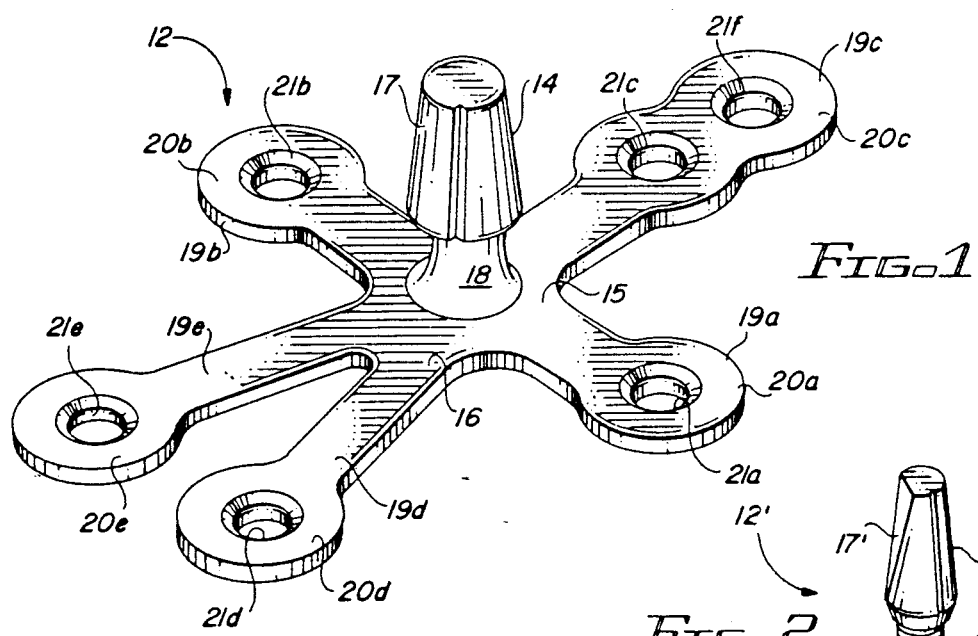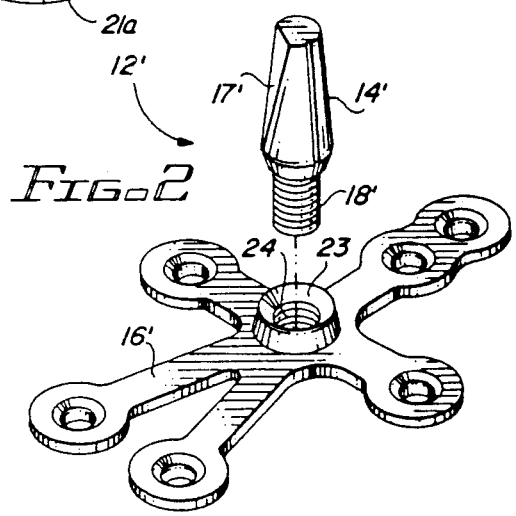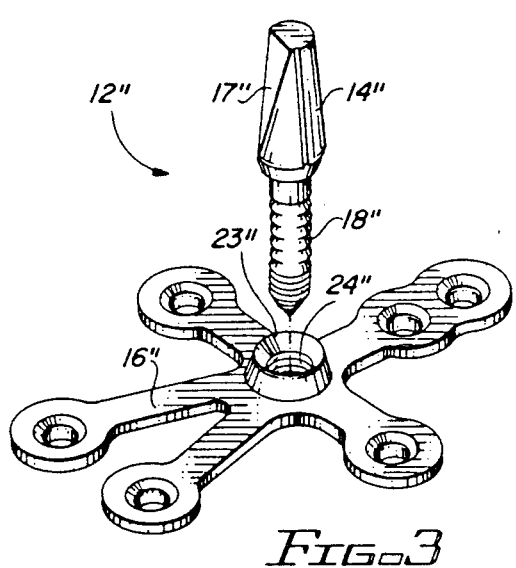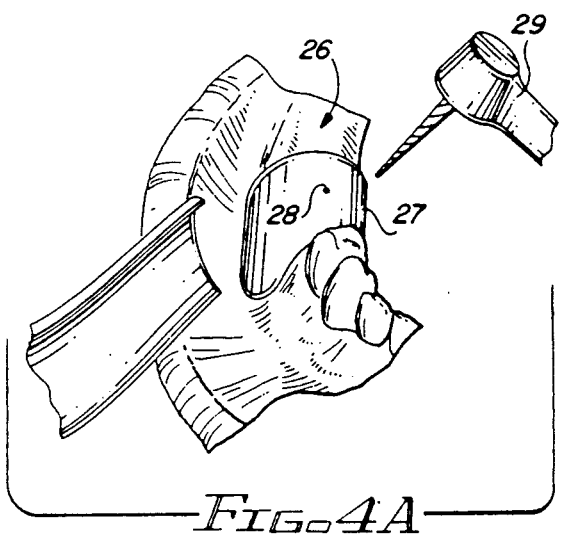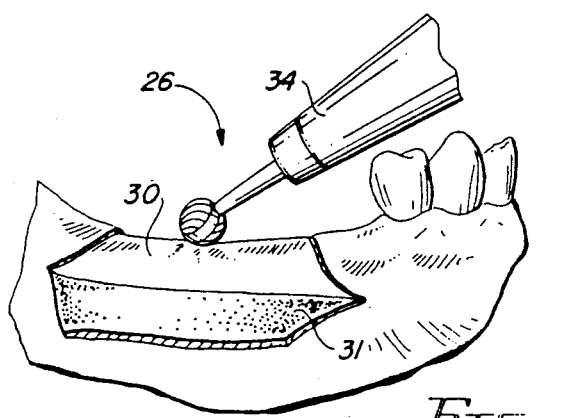

DENTAL IMPLANT AND METHOD OF IMPLANTATION

This is a continuation-in-part of application Ser. No. 07/442,471, filed Nov. 22, 1989, now abandoned; which is a continuation of application Ser. No. 07/356,271, filed May 24, 1989 now abandoned. The disclosures of those applications are incorporated herein by reference thereto.

BACKGROUND OF THE INVENTION

This invention relates, in general, to a dental implant for use in maxillo-facial surgery; and, in particular, to a juxtaosseous implant universally applicable at an implantation site on the mandible or maxilla, and to a method of surgical implantation using such an implant.

A dental implant of the type to which the present invention relates is intended to function as a bond between a dental prosthesis, such as a crown or bridge, and one of the mandible and maxilla facial bones. It is normally desired that such bond be permanent. A dental implant is subject to many varied and frequent stresses, often of considerable magnitude. So it is important that the connection between the implant and the bone be strong and secure.

Long term success of the bone-to-implant connection requires good biological acceptance resulting in tissue scarification, as well as good biomechanical adaptation resulting in consolidation. The desired result is a stable and sufficiently strong mounting taking into account the maxim in bone surgery that: "the stability of a mounting is indispensable for the formation of good bone callus; and, conversely, good bone callus ensures good stability." Failure in about 15% of dental implants is synonymous with osteolysis.

As a dental implant is intended to replace the natural bond between a tooth and the bone, it must be able to withstand the same stresses to which the natural connection between a tooth and the bone would be subjected. The stresses derive from forces applied through the prosthesis onto the implant which transmits them to the bone. In order to obtain good consolidation, it is desirable that the stresses transmitted to the bone by the implant be as close to normal as possible in order to avoid disadvantageous restructuring of the bone in adherence to Wolf's law. To avoid parasitic stresses, the dental implant should also not have any abnormal mobility. Thus, it is desirable that the implant have a stable, or even better, a hyperstable, seating from the onset. This means that the implant should be designed for immediate adequate permanent placement. Furthermore, taking into account the interaction between the bone and the implant, research has shown that good quality bone callus makes it desirable for the pericortex and the implant to constitute a coherent mechanical entity.

As with other bones, the mandible and maxilla each have two types of bone tissue: the cortical and the cancellous. The cortical bone is the hard and compact external casing that has a dense structure composed of osteons assimilable to fibers. The cancellous or trabecular bone is soft and spongy, and covers the internal faces of the cortical bone. Cancellous bone is made of superimposed lamellae, comparable to plywood.

Mechanical Considerations

An understanding of mechanical characteristics of bone is relevant to development of a useful implant. The mechanical "performance" under simple solicitation (traction, compression, torsion, shearing, flexing) of cortical bone is about 30 times superior to that of cancellous bone, and energy absorption is about 40 times less. Bone absorption is also different depending on the layer. The lamellar bone absorbs more energy than the haversian compact bone, and the subperiosteal bone more than the lamellar endosteal bone.

Cortical bone has a better resistance to compression and flexion, but a lower resistance to shearing forces than cancellous bone. The least mineralized subperiosteal lamellar layer in the cortical bone absorbs the most energy. When cortical bone is highly mineralized, it absorbs less energy. The resistance of cortical bone is due mainly to elastic deformation (like a spring).

Cancellous bone has little mechanical value, which diminishes dramatically with age. Its compression resistance is proportional to its apparent density. The mechanical value of cancellous bone resides in its role as a hydraulic shock absorber through the blood filled cavities.

The mandible is a bone of endochondral origin (Meckel cartilage). It is mobile, suspended at the base of the skull, made up of trabecular bone, and covered by a highly resistant cortical envelope. It has a strong outer surface surrounding a honeycomb structure. It is a typical composite entity with an elastic structure, i.e., the cortical bone, and a structure which disperses, absorbs and transmits stresses, i.e., the cancellous bone. The mandible is an elaborate ensemble which can autonomously absorb great stresses, to be integrated into the concept of composite beam bone-muscle: the muscles acting by: guying the bone; increasing the pre-stresses; and harmonizing the compression stresses. For all these reasons, the mandible can be considered as an ideal site for implantation.

The maxilla is a bone of membranous origin, which is even and symmetrical. It is attached to the base of the skull by fragile structures, and is pitted with numerous cavities. The maxilla is made up of very fragile fascicular bone and by stretches of trabecular bone covered by cortical bone. The region of the sinus can be considered as a mechanical no-man's land. As a rudimentary structure, it does not absorb stresses, but guides, diffuses and deflects them.

The stresses picked up by the teeth are transmitted by the intermediary of the bone trabeculae to more distant integrating structures. The bones relevant to dental implantation are mainly subjected to vertical and horizontal forces. The vertical forces have a slightly mesial direction, and are primarily produced by mastication occurring approximately 1500 times per day and by swallowing occurring approximately 500 times per day. The intensity of the forces varies according to age, muscular strength and dental condition. Their magnitudes vary from 60 DaN on the molars to around 20 DaN on the incisors, but decrease by 50% according to the alimentary bolus and edentation.

For our studies on dental implants, we chose the following medium values: 30 DaN for the molars and 10 DaN for the incisors. These forces are of rapid onset and are brief.

The vertical forces produce stresses of compression, with the stress being defined by $$P + F/S$$

where "S" represents the surfaces of the alveola-dental ligaments taken as 200 mm² for an incisor and 450 mm² for a 2nd molar. This gives us approximately the following values: 0.05 DaN/mm² for the incisors and 0.07 DaN/mm² for the molars.

Horizontal forces are mainly developed by the tongue ("lingual forces"), occurring about 500 times per day. They are variable and do not exceed a few DaN. We considered a medium value of 3 DaN. The onset of the horizontal forces is slow and their duration is more significant than that of the vertical forces. They create shearing stresses at the level of the implant, particularly in the anterior and anterior-lateral sectors.

The mechanical functions of the alveolar-dental ligament are the following: Sharpey's fibers decrease the stress through the elasticity of the collagen. The abundant vascularization of the ligament has the effect of a hydraulic shock absorber. The periodontal ligament is a viscoelastic structure. Recent research has shown that the bone and the periodontium form a double viscoelastic structure. In the totally edentulous patient, the periodontium with its alveolo-dental ligament is absent.

A dental implant will undergo certain stresses: brief compressions, increasing when approaching the molar region; and shearing and torsion, which is slow and drawn out increasing when approaching the median line. The implant, in the absence of the viscoelastic structure, will directly transmit the stresses at the bone level. It is a desirable objective in developing an implant that these stresses be decreased by the form, the surface, and the mobility of the implant, as well as by the mechanical characteristics of the material used for the implant. The release of parasitic stresses due to a mechanical conflict between the bone and the implant in certain anatomical regions should be avoided.

Depending on the osteoarchitecture and stresses, one can deduce the risk zones and the secure zones. The mandibular molar and premolar regions are very propitious for implants. The mandibular canine and incisory regions are reliable. The maxillary molar region as well as the incisory region are acceptable. The maxillary canine and premolar regions are the most susceptible to complications.

It is a desirable objective that a dental implant should restore the physiological stresses in order to respect Wolf's law. The challenge in implantology is to be able to place the implant, while immediately restoring a function that ceased to exist.

The bone is capable of supporting considerable stress. Excess stress results in osteolysis through crushing of the fibers and the bone trabeculae, and crushing of the vessels leading to vascular thrombosis. The latter leads to a devascularization, followed by a decrease in oxygen pressure resulting in cellular bone death. The subsequent appearance of microgeodes leads to osteolysis. As the peri-implant retention diminishes, loosening occurs leading to an abnormal mobility of the implant. Its corollary is the increase in compression and shearing stresses. Once the vicious circle has begun, it can end in invasive osteolysis. A desirable goal in placing an implant is, thus, to respect Wolf's law and not to create parasitic stress.

Wolf's law may be stated as: "the structure of a bone depends on its function and all changes in its function lead to a modification in its structure." The onset of new stresses in a bone, reorients the bone trabeculae, resulting in a mechanical weakening during several weeks. To correctly consolidate, the bone needs to receive mechanical solicitations which reorient the new bone trabeculae during the osteoblastic phase of the peri-implant bone callus.

Conventional Implants

Conventional dental implants have not done an adequate job in meeting the objectives set out above. Wide usage is made of endosseous implants which are inserted in the bone after it has been bored. Such implants typically comprise a post mounted on a threaded shank that simply screws vertically down into the crestal portion of the bone, thereby delivering forces applied vertically to the prosthesis directly vertically down into the underlying cortical and cancellous regions, with resulting lamellae reorientation taking place that is not only deleterious to the bone but leads to poor seating that is eventually disrupted. The result is that the implant is not permanent. Endosseous implants also take the form of posts supported on vertically oriented blades that are deposited for osseointegration in the bone, and have similar shortcomings.

Attempts have been made to mount a post with a juxtaosseous structure that extends down and to the buccal (cheek side) and lingual (tongue side) surfaces of the bone, so that the vertical forces are dissipated laterally. Examples of such pericortical arrangements are shown in Hubert et al., French Patent 2,138,224 and Sampson U.S. Pat. No. 3,579,829. The Sampson implant takes the form of an inverted U-shaped clamp, having a truncated conical mounting post secured on a pedestal and two, opposing, downwardly directed, laterally-spaced rigid plates that are drawn together to drive spikes into the bone. The Hubert et al. implant takes the form of a molded metal grille including a plurality of posts joined together by metallic bands. Such conventional juxtaosseous arrangements are, however, site dependent and lack the versatility and flexibility for universal placement at both nasal (front) and distal or lateral (rear) sites throughout the mandible and maxillary dental arcades.

Desirable Implant Characteristics

Our research has concluded in the development of an implant supported by the subperiosteal trabecular bone, which has the following characteristics: a stable connection with the bone; freedom from abnormal mobility so as not to create parasitic stresses; diffuses energy in the cancellous bone by the intermediary of its attachment points; and, constitutes a coherent mechanical entity with the bone.

In order not to create excessive stresses, the dental implant should be stable. Abnormal mobility increases the stresses of compression and shearing. Its stability can be achieved by different means, particularly through its surface and the mounting.

The stress being defined by $P = F/S$, P can be decreased by increasing the surface of the implant, thus justifying, from a mechanical point of view, a juxtaosseous implant over an endosseous implant because of a larger available surface area. The same reasoning underlies the use of a multidirectional implant and screws with greater developed surfaces than available for endosseous implants. For example: when implanting with a screw of 4 mm in diameter (maximum possible in the maxilla), the screw must reach at least 15 mm into the bone in the incisor region (surface of the previous ligament 200 mm²). The same kind of implant in the molar region would require a depth of at least 30 mm which is anatomically impossible.

The implant must not be too voluminous because: the amount of bone to be removed is considerable; the female form is difficult to implement; the devascularization at the time of placement is significant, including the risk of a higher bone resorption during the days and weeks after the placement; the more voluminous the implant, the more it reaches into the cancellous bone which has poor mechanical qualities; in case of removal for reasons of loosening, the damage done to the bone is much greater; whereas one of the essential stipulations in dental implantology is the "restitution ad integrum" in case of failure.

The implant mounting must be stable from the beginning and must remain stable in spite of the physiological periimplant bony resorption. It is a triport like "Eiffel Tower" mounting which best opposes the existing stresses and does not create pathological stresses in the bone. This procedure has been successfully used in long bone surgery (Ender's nailing, fascicular pinning) due to its blocking effect inside the bone and the multidirectional diffusion of stresses. It is a stable mounting in the three spacial dimensions and in rotation. A dental implant, like all other bone implants, must be positioned in such a way as to obtain a sufficient load, without abnormal stresses.

We have studied the biomechanics of the mandible and defined the site of the neutral fiber or fiber of stress neutrality in order to determine the ideal line of osteosynthesis. At precisely this level, the load on the material is minimal while the bony pieces are being supported. The stabilizing screws of the implant should be placed exactly alongside this neutral fiber. At the maxilla, the screws should be placed on the level of the roots of the pillars where there are zones of cortical bone.

In bone surgery, the screw is the most efficient method of holding pieces together. This procedure has been used for almost a century. Such placement has the advantage of immediate retention through the threading, except for rotation, and increase of the contact surface by virtue of the threads.

Maxillar implantology is subject to certain basic rules regarding screws: The endosseous portion should be longer than the protruding portion. The peripheral retaining bone should be at least equal to half the diameter of the screw; for example, when using a screw 4 mm in diameter, the peripheral bone should be at least 2 mm thick. This restricts its use in the maxilla where the edentulous bone has the shape of a sabre blade. The use of a dynamometric screwdriver is strongly advised in order not to fracture the threading. We have studied the torque that would destroy the threading in the mandibular cortical bone 7 DaN×cm, the optimum torque being 5 DaN×cm. For facial bones tapping is unnecessary, even dangerous, as it maximizes trauma especially in the maxilla. The use of self-tapping screws is, thus, logical.

Implant and bone should constitute a coherent mechanical system. The implant should be stable, sufficiently sturdy and positioned in the appropriate site without increasing the rigidity of the bone.

We believe that a rigid material leads to a good deviation of the forces. In the presence of a rigid plate, the trajectory of the tension lines passes through the plate and not through the bone. The bony segment beneath the rigid plate is no longer solicitated in a manner which leads to structural changes of the bone in the form of osteoporosis and atrophy. This phenomenon is called the "Shield effect."

Woo in *8 J. Biomed. Mater. Res.* 321 (1974) concludes in his study that the comparison between the characteristics of the bone and osteosynthesis material can be expressed by the material/bone ratio which should be between 1 and 2 in order to achieve good bone callus. For most commercial materials used in bone implantology, the ratio is between 6 and 8, thus furthering the onset of osteoporosis. The same can be said of most of the dental implants.

In summary, several years of research have led us to invent an implant with the following characteristics: It interfaces with the cortical bone and is supported by the subperiosteal lamellary bone by means of several small screws. By virtue of these screws, it diffuses the stresses in the cortical and the cancellous bone. Its form is multidirectional. The mounting at the bone level has the advantages of the tripod like "Eiffel Tower" mounting. It is made of titanium T 40, or other biocompatible material chosen with mechanical characteristics quite similar to those of the cortical bone. Its placement causes a minimum of bone lesions. And, it can be employed at any site on the mandible or maxilla to replace any tooth, i.e., it has universal application.

None of the implants now actually on the market is really stable in the three spacial dimensions and in rotation. The juxtaosseous implant is, from a mechanical point of view, the most logical solution o condition that it is stabilized through several attachment points acting along different directions. The mounting of the dental implant of the invention is hyperstable. The characteristics of bone and implant are chosen to be close, so that the mounting is isoelastic. The hyperstability and isoelasticity of this implant allow an almost immediate loading of the mandible and a very early loading of the maxilla.

SUMMARY OF THE INVENTION

It is an object of our invention to provide an improved dental implant of the juxtaosseus type, possessing the desirable characteristics delineated above. Another object of our invention is to provide an improved process for the placement of a juxtaosseous implant, bonded by means of osteosynthesis.

In accordance with one aspect of the invention, a dental implant is provided for use as a bond between a dental prosthesis and the mandible or maxilla bone that has a central post projecting upward from a spider-like base having a central hub region and a plurality of spoke-like branches extending radially outward at angularly-spaced intervals from the hub region. The branches can be cut or bent to conform the implant to the contours of the implantation site, and then secured at terminal screw mount ends to buccal and lingual bone portions to effect fixation.

In a preferred embodiment, the implant has five branches, extending outward respectively at 0°, 90°, 160°-170°, 190°-200° and 270° positions from the hub, with the 90° and 270° branches being shorter than the 0° branch, and the 160-170° and 190°-200° branches being longer than the 0° branch. A preferred material for the implant is a titanium alloy. Unitary and separable post versions of the implant are described.

Another aspect of the invention is a process for the implantation of the improved implant.

BRIEF DESCRIPTION OF THE DRAWINGS

Embodiments of the invention have been chosen for purposes of illustration and description, and are shown in the accompanying drawings, wherein:

FIG. is a perspective view of a dental implant in accordance with the invention;

FIGS. 2 and 3 are exploded views of modified forms of the dental implant of FIG. 1;

FIGS. 4A-4G are views showing the steps in a method of implantation according to the invention, utilizing a dental implant as in FIG. 1;

Throughout the drawings, like elements are referred to by like numerals.

DETAILED DESCRIPTION OF PREFERRED EMBODIMENTS

Figure 4C:
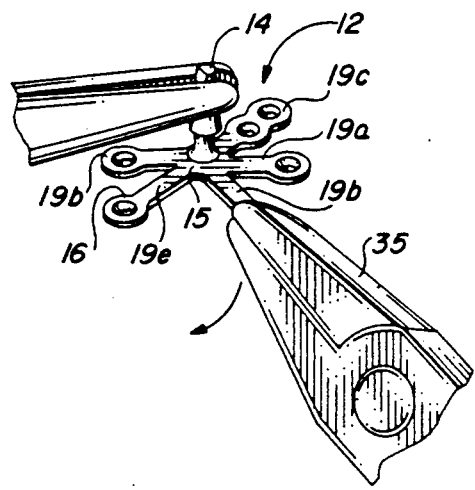

The principles of the device and method of the invention are illustrated, by way of example, with reference to an embodiment of dental implant 12 (FIG. 1) which can be implanted in accordance with the steps of an embodiment of a maxillo-facial surgical procedure discussed further below (FIGS. 4A-4G).

The implant 12, as shown in FIG. 1, comprises a post 14 connected to and extending upward from a central region 15 of a thin planar base 16. The post 14 has a truncated cone-shaped top portion 17 integrally formed coaxially above a generally hyperbolic cone-shaped bottom portion 18 that tapers first inwardly from the bottom of portion 17, then outwardly toward the plane of the base 16, in smooth, continuous fashion. The top portion 17 may be axially ribbed or similarly roughened and is shaped in accordance with known principles to provide a suitable platform for the seating a dental prosthesis, such as a crown or bridge support (not shown).

The base 16 of the implant 12 is spider-like in configuration giving a general, tripod-like Eiffel Tower appearance to the mounted implant. The base 16 comprises the central region or hub 15, from which extend radially outward a plurality of three or more branches or legs 19 in spoke-like fashion, as shown. The implant 12 preferably has five branches 19a-19e, with two short branches 19a, 19b extending outwardly at diametrically opposite, 90° and 270° positions respectively as viewed looking down the post axis. A medium-length branch 19c extends outwardly in the 0° position, at right angles to each branch 19a, 19b; and two long branches 19d, 19e extend outwardly generally opposite the branch 19c. The branches 19d, 19e are respectively separated by an acute angle (e.g., 20°-40°) and are preferably positioned at approximately the 160°-170° and 190°-200° positions.

The base 16, and preferably also the post 14, is made of a biocompatible material, such as a titanium alloy (viz. titanium T40), which has mechanical characteristics that closely match those of the cortical bone of the mandible and maxilla. For reasons which will become apparent from the description of the implantation methodology below, the material (at least at the branches 19) should be sufficiently malleable to permit bending under manual force applied through hand tools, and be sufficiently fatigue-resistant to permit bending and unbending without breaking for a reasonable number of repetitions. The material should also be sufficiently cuttable to permit intentional severing, when desired, using simple handheld cutting tools. The post 14 must be formidable enough to maintain a stable connection to the base without undesired deformation or deflection when the overlying prosthesis is subjected to normal mastication and tongue induced force. If titanium fibers rather than volutes are used, it is recommended that the fibers be axially aligned with the branches to minimize unintentional sectioning.

Each branch 19 is an elongated strip of material having a proximal end integrally connected with the hub 15 and a distal end integrally connecting a screw mount terminal 20. The shown terminals 20a, 20b, 20d, and 20e have identical round, disc-like forms and each includes a central axial bore hole 21, surrounded by an annular portion, which serves as an attachment hole for passage therethrough of a fastener, such as the shank of a threaded screw, discussed further below. The purpose of the annular portion of the terminals 20 is to act as a platform for retention of the distal end of the associated branch 19, when the implant is fixed to the bone. The terminal 20c serves the same function with respect to the branch 19c, but preferably has a flat, figure-eight shape, as shown, presenting two radially-spaced holes 21c, 21f through which screws or other fasteners may be passed during fixation.

FIGS. 2 and 3 illustrate modified embodiments of implants 12', 12" in accordance with the principles of the invention. The implant 12' has the same general configuration as the implant 12, except that the post 14' is formed as a separate component from the base 16'. The secure joinder of the post 14' to the base 16' is accomplished by providing an upwardly projecting socket 23 with an internally threaded bore 24 centrally on the upper surface of the base hub 15, and forming the bottom portion 18' of the post 14' with a depending externally-threaded stem that can be interengaged with the bore 24 coaxially of the socket 23. The sides of the socket 23 are externally sloped to match the contour at the bottom of the post 18. The top of the socket 23 is provided with a concavity for receiving the lower part of an inwardly tapered juncture between the post top portion 17' and the post bottom portion 18'. When the post 14' is securely threaded into the socket 23, the implant 12' will function the same as the implant 12.

The implant 12" shown in FIG. 3 differs from the implant 12' of FIG. 2 only with respect to the configuration of the post 14". Post 14" has an extended length of its bottom portion 18" which is designed to function, not only to join the post 14" to the base 16", but also to extend beyond a coaxial throughbore 24" into the bone itself. The post bottom portion 18", thus, functions to vertically secure the post 14", if desired, as in conventional endoosseal vertical post anchoring techniques, in addition to the laterally directed anchoring technique of the invention. This is not currently seen as the preferred implementation, but may provide a measure of comfort to oral surgeons more familiar with the conventional vertical anchoring approach.

FIGS. 4A-4G illustrate an embodiment of surgical implantation procedure utilizing a dental implant, such as the implant 12 of FIG. 1.

As a first step in the fixation of an implant 12 at a desired implantation site 26, such as the site of a lateral molar of the mandibular dental arcade, a temporary prosthesis 27 is applied to identify the desirable point 28 of emergence of the post 14 of the intended implant 12 (FIG. 4A). The point 28 is located in known way, such as by use of a probe or other pointed dental tool 29.

Once the point of emergence is established, the distal region of the mandible 30 is surgically exposed at the site 26 by cutting the oral epithelium and folding the buccal and lingual gum flaps 31, 32 back. The crestal bone portion is then trimmed at the point 28, using a bur, rasp of similar shaping tool 34 to prepare the site 26 to serve as a substrate for receiving the undersurface of the hub 15 of the implant 12 (FIG. 4B).

Figure 4D:
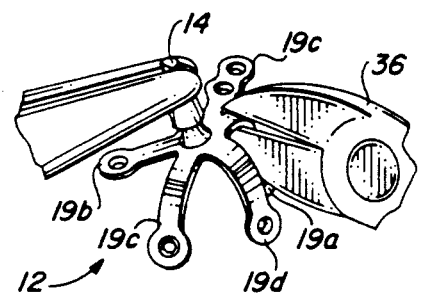

The branches 19 of the implant 12 are then bent and shaped according to the anatomy of the bone. FIG. 4C shows the bending of one of the branches 19d on the supported implant 12, by gripping its terminal end 20d with a pair of needle-nosed pliers 35 moved downwardly in the direction indicated by the arrow. For the particular site 26 shown, the branches 19c and 19e are likewise bent in a downward direction away from the post 14. As with the bending, one or more of the branches 19 may be sectioned as shown in FIG. 4D, such as by means of cutting pliers 36. For the chosen site 26, the branch 19a may be cut. The jaws of the pliers 36 are preferably made of the same material as the implant 12.

The implant 12 is next positioned on the exposed bone 30 at site 26 (FIG. 4E), and readjustments are made to the bent configurations of the unsectioned branches 19b-19e to conform the shape of the underside of the base 16 to the external shape of the crestal bone 30. The surface of the bone 30 may be further smoothed (see FIG. 4B), if irregularities or ridges exist. The bone may also be striated in axial alignment with the placement of the branches to increase patient comfort and minimize lateral displacement of the branches.

Figure 4E:
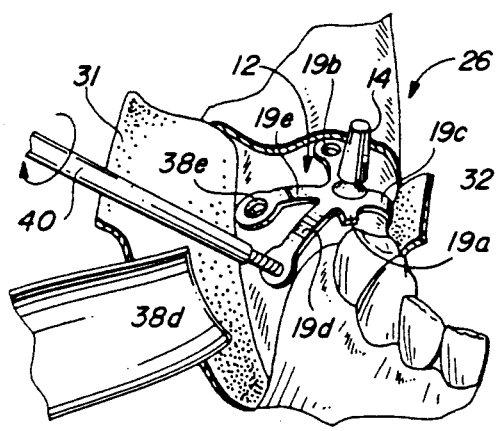
Figure 4F:
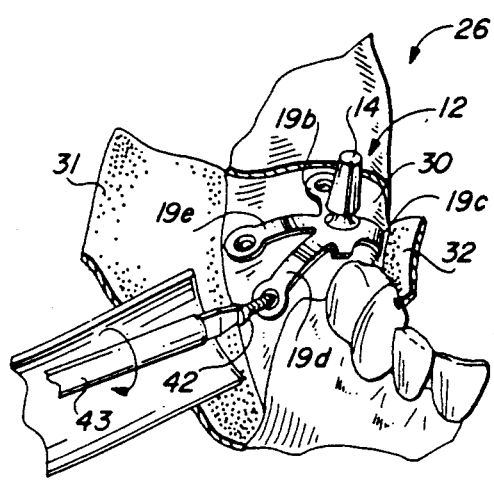

Once the implant 12 is shaped to match the configuration of the prepared bone site 26, holes are drilled into the bone at points 38 determined by the locations of the boreholes 21 in the implant 12 (FIG. 1). The drilling of the holes in the bone 30 can be made with a drill handpiece 40, rotated at a speed preferably not exceeding 1500 r.p.m. (FIG. 4E). The implant is then fixed to the bone 30 by means of screws or rivets 42 which are brought through the holes 21 of the terminals 20 of the branches 19 and into the drilled bone holes 38 by manual rotation of a screwdriver 43 (FIG. 4F).

Figure 4G:
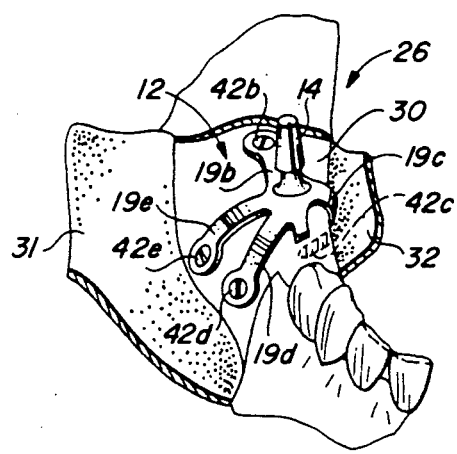

The implant 12 is shown in FIG. 4G after fixation at the site 26 to the bone 30. Screws 42b-42e are shown respectively brought through the bores 21b-21e of the implant 12. The screw 42c may also be brought through the hole 21c, if the anatomy makes that more appropriate.

The implant 12, fixed as shown, is joined into the bone 30 at connection points remote from the post 14. Because of the stiffness of the implant 12, forces due to lingual articulation and mastication applied to the prosthesis and into the post 14 will be shielded from the point 28. The radial extensions of the branches 19 will ensure that the forces will be transmitted to the bone 30 by directing them laterally along desired stress lines, so that Wolf's law will not apply to weaken the bone connections.

FIGS. 5-10 illustrate alternative fixation approaches for the same implant 12.

Figure 5:
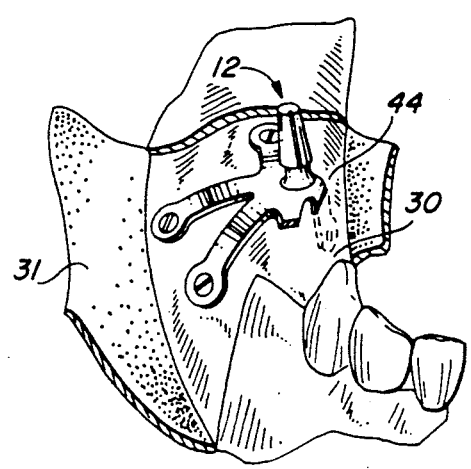
FIGS. 5-10 are views showing fixation of the implant in variations of the method of FIGS. 4A-G, FIGS. 5-7 and 9 corresponding to the view of FIG. 4G and FIGS. 8 and 10 being section views taken along the lines 8-8 and 10-10 of FIGS. 7 and 9, respectively.

In FIG. 5, the lingual connection of branch 19c is established by fitting the branch 19c, without a screw 42 into a bore 44 made in the lingual face of the bone 30.

Figure 6:
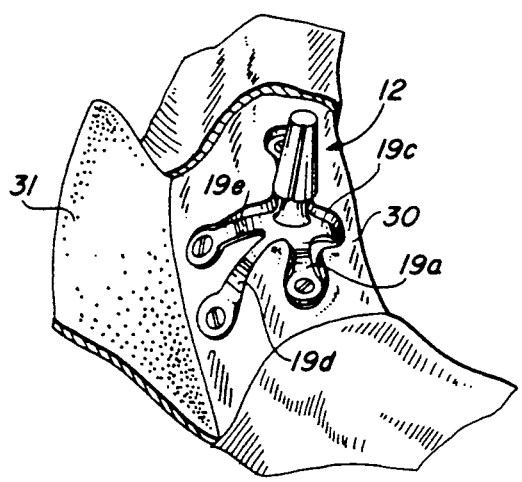

FIG. 6 illustrates the placement of the implant 12 after the bone 30 has been recessed to accommodate the implant 12. In the shown arrangement, the branch 19a is left uncut and the branch 19c, opposite the branches 19d, 19e is cut.

Figure 7:
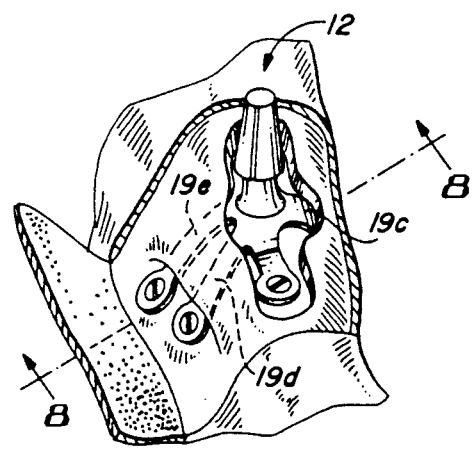
Figure 8:
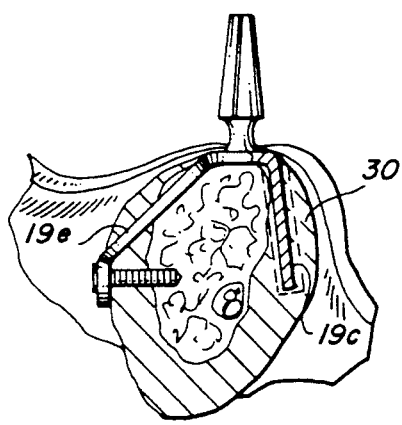

FIGS. 7-8 illustrate a method of fixation wherein the branches 19d, 19e are tunneled below the surface of the bone 30. This has the advantage that forces on the post 12 causing radial stresses on the base 16 will encourage lamellae to form in a direction parallel to the tunneled bone surface.

Figure 9:
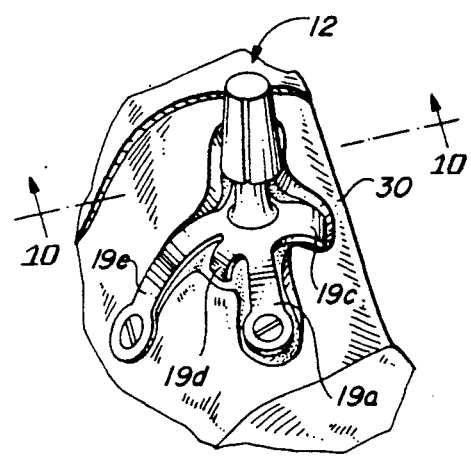
Figure 10:
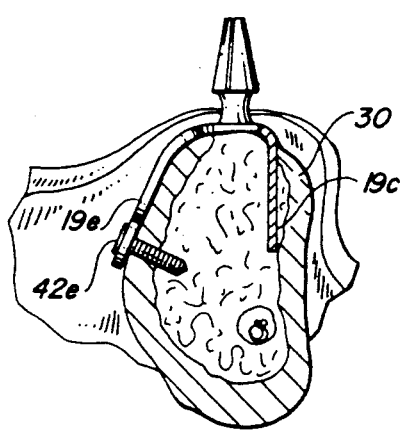

In FIGS. 9-10 the clipped ends of branches 19c, 19d are directed into the bone 30 and the other branches 19a, 19b (not shown in FIG. 9) and 19e are attached by means of screws.

Figure 11:
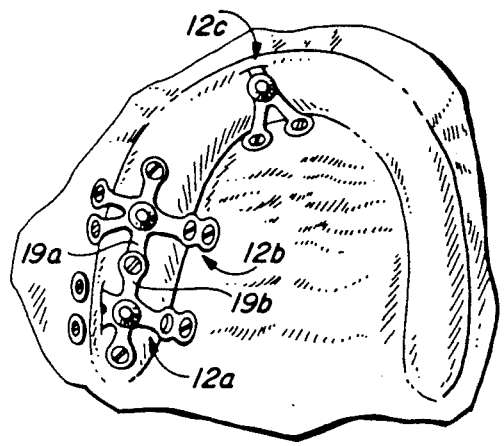
FIG. 11 is a schematic view illustrating the universal implementation of the invention at various tooth locations.

As shown in FIG. 11, two implants 12a, 12b are shown joined at adjacent sites by a common screw passed through superposed branches 19a, 19b. An implant 12 (see implant 12c) is also suitable for implantation at an incisor location of the mandible. Similar implantation can be performed for the maxilla bone.

The screws which are preferably made of the same metal (titanium) as the implant. They are 5 mm and 7 mm long and are self tapping. Rivets may be used in place of the screws.

Suitable tools for surgical implantation of the implant include a 1.5 mm diameter drill; implant holding pliers; implant bending pliers; cutting pliers; a prehensive screwdriver; and an ordinary screwdriver.

Experimentation and Clinical Experience

Experimental testing of the implant and implantation procedure was carried out in the following manner:

In the first phase, a biomechanical engineer calculated the different forces and stresses exerted in all areas of the implant, post, socket and branches, in relation to the known, previously described, vertical and horizontal forces. He determined that the characteristics of titanium T40 were appropriate to resist the existing stresses. He also determined that the vertical and horizontal forces were transmitted on the level of the connections (i.e., at the screws) and that those exerted uprooting and shearing forces at the level of the periimplant bone interface. The extraction forces were found to be notably less (approximately 10%) than bone fracturing forces. A second phase, theoretical study, using a computer model, confirmed the results of these calculations.

In the third phase, several prototypes in titanium TA6 V4 and titanium T4 were manufactured and dynamic tests on models of different types of wood and sheep bone were carried out. These tests showed that there was dismantling of the system only when the traction forces in the axis of the post were superior to 100 DaN. Titanium T40 was selected as the preferred material. Several prototypes of the invention implant in which the branches were of different thickness (from 0.6 mm to 0.35 mm) were tested on dry human bones (mandible and maxilla) and then studied. The mountings appeared stable in traction up to 60 DaN in maxillar application and 100 DaN in mandibular application. A thickness of 0.45 mm for the branches of the implant and screws of 5 mm and 7 mm in length were chosen as suitable.

During the last, fifth phase, tests with several definitive prototypes were carried out on a fresh human mandible. No dismantling (with 4 screws) of the implant was witnessed, despite a traction force of 100 DaN.

In clinical testing, implants have been installed on male and female patients at various implantation sites with a success rate of 80% based on observations to date.

As can be appreciated from the foregoing, the implant and implantation procedure of the invention provides an implant which is multi-directional and which is attached by at least three points to the cortical bone, thus making it hyperstable. Stresses passed to the implant are diffused in the cancellous bone along three directions by virtue of the attachment points. A preferred material for the implant is titanium T40, which is known not only for its excellent biocompatibility but also for its mechanical qualities close to those of the cortical bone. The implant is easily placed with a minimum of bone lesions. It can replace any tooth and thus has universal application. Placement is done with the aid of only a few simple tools. The implant can be used either as a solid unit (with immediate loading) or in two stages for a delayed loading. The implant can be bent/prepared at the time of insertion, partially prebent/prepared based on implantation site, or more precisely prebent/prepared based on a mold of the site.

It will be appreciated by those skilled in the art to which the invention relates that various substitutions and modifications can be made to the described embodiment without departing from the spirit and scope of the invention as described by the claims below.

What is claimed is:

1. A dental implant for use as a bond between a dental prosthesis and the mandible or maxilla bone at an implantation site having crestal, buccal and lingual bone portions, said implant comprising:
   a spider-like base of a material, said base having a central hub region and at least three spoke-like branches extending radially outward at angularly-spaced intervals from said hub region; and
   a post projecting upward from said base at said hub region, and dimensioned, configured and adapted to mount the dental prosthesis thereon;
   said hub having a plate-like undersurface dimensioned, configured and adapted to be placed over said crestal bone portion at said implantation site;
   said branches comprising elongated strips having proximal ends integrally connected with said hub region, and distal ends including means for individually securing said distal ends to said bone; and
   said branches being dimensioned, configured and adapted, and said material and angularly-spaced intervals being chosen, so that said hub undersurface can be placed over said crestal bone portion and said branches can be drawn longitudinally and bent downward about said implantation site to individually secure them with said securing means at points of attachment to said buccal and lingual bone portions, for establishing a three-point tripod-like connection of said base to said site, providing stability in three spatial directions and against rotation, with said hub region shielding said crestal portion from vertical and
   horizontal forces applied to said post due to the action of mastication and lingual articulation on the received dental prosthesis, and said branches dissipating said forces by dispersing them in multiple directions radially away from said hub region, longitudinally along said branches to said points of attachment.

2. A dental implant as in claim 1, wherein said means for securing comprises a disc-like screw mount terminal having a bore and an annular region surrounding said bore for securing said branch distal end to said bone by receiving a shank of a fastener through said bore.

3. A dental implant as in claim 2, wherein said angularly-spaced intervals are chosen so that first and second of said branches are spaced by an acute angle from each other and are generally diametrically opposed to a third branch.

4. A dental implant as in claim 3, wherein said third branch extends outward from said hub region at a 0° position, and said first and second branches extend outward at positions between 135° and 225°;

5. A dental implant as in claim 4, wherein said first and second branches extend outward at positions of 160°–170° and 190°–200°, respectively.

6. A dental implant as in claim 3, wherein said base further comprises fourth and fifth branches which are diametrically opposed to each other and which extend generally at right angles to said third branch.

7. A dental implant as in claim 6, wherein said first and second branches are longer than said third branch, and said fourth and fifth branches are shorter than said third branch.

8. A dental implant as in claim 7, wherein said means for securing comprises a disc-like screw mount terminal having a bore and an annular region surrounding said bore for securing said branch distal end to said bone by receiving a shank of a fastener through said bore.

9. A dental implant as in claim 8, wherein said screw mount terminal of said third branch has a figure eight configuration including two radially-spaced bores and two radially-spaced annular regions respectively surrounding said bores.

10. A dental implant as in claim 9, wherein said branches extend outward from said hub region at 0°, 160°–170°, 190°–200°, 90° and 270° positions, respectively.

11. A dental implant as in claim 10, wherein said post and base comprise separate elements and said implant further includes means for interconnecting said post and base separate elements.

12. A dental implant as in claim 11, wherein said hub region further comprises a socket with an internally-threaded bore centrally positioned on said hub region, and said post has a bottom portion, externally-threaded for interengagement with said socket bore.

13. A process for the implantation of a dental implant on the mandible or maxilla bone at an implantation site having crestal, buccal and lingual bone portions, said implant comprising a spider-like base having a central hub region including a plate-like undersurface, and at least three spoke-like branches extending radially outward at angularly-spaced intervals from said hub region, said branches comprising elongated strips having proximal ends integrally connected with said hub region and distal ends; and a post projecting upward from said base at said hub region, said post being dimensioned, configured and adapted to mount the dental prosthesis thereon; said process comprising the steps of:
   shaping said implant by drawing said branches longitudinally and bending at least some of said branches downward to conform said implant to the configuration of said implantation site;

placing said hub region undersurface over said crestal bone portion at said site;

individually securing said distal ends of said branches at points of attachment to said buccal and lingual bone portions to establish a three-point tripod-like connection of said base to said site, providing stability in three spatial directions and against rotation, with said hub region shielding said crestal portion from vertical and horizontal forces applied to said post due to the action of mastication and lingual articulation on the received dental prosthesis, and said branches dissipating said vertical and horizontal forces by dispersing them in multiple directions radially away from said hub region, longitudinally along said branches to said points of attachment.

14. A process as in claim 12, wherein said securing step comprises fastening said at least three branches so that a first branch is fastened to said lingual portion, a second branch is fastened to said buccal portion, and a third branch is fastened to either said lingual or said buccal portion at a point of attachment spaced from said point of attachment of said fastened first or third branch fastened to the same portion.

15. A process as in claim 14, for the implantation of an implant having disc-like screw mount terminals at said branch distal ends, said screw mount terminals having bores and annular regions surrounding said bores, wherein said securing step comprises fastening said terminals to said bone by passing screws through said bores of a plurality of said bent branches.

16. A process as in claim 15, wherein one of said branches is fastened to said buccal or lingual portion by tunneling through said portion.

* * * * *